(12) United States Patent
Potter et al.

(10) Patent No.: US 7,973,034 B2
(45) Date of Patent: Jul. 5, 2011

(54) AMIDE, ARYL SULFONAMIDE, ARYL UREA, AND α,β-DIKETONE DERIVED CARBOXYLESTERASE INHIBITORS, AND THEIR METHODS OF USE

(75) Inventors: Philip Michael Potter, Memphis, TN (US); Janice Louise Hyatt, Memphis, TN (US); Christopher Lee Morton, Memphis, TN (US); Paul P. Beroza, Redwood City, CA (US); Komath V. Damoradan, Cupertino, CA (US)

(73) Assignee: St. Jude Children's Research Hospital, Memphis, TN (US)

( * ) Notice: Subject to any disclaimer, the term of this patent is extended or adjusted under 35 U.S.C. 154(b) by 582 days.

(21) Appl. No.: 12/032,344

(22) Filed: Feb. 15, 2008

(65) Prior Publication Data

US 2008/0146548 A1    Jun. 19, 2008

Related U.S. Application Data

(62) Division of application No. 10/925,367, filed on Aug. 24, 2004, now abandoned.

(60) Provisional application No. 60/498,778, filed on Aug. 29, 2003.

(51) Int. Cl.
*A61K 31/55* (2006.01)
(52) U.S. Cl. .................................. 514/220; 514/617
(58) Field of Classification Search .................. 514/220, 514/617
See application file for complete search history.

(56) References Cited

U.S. PATENT DOCUMENTS

| 4,046,918 A | 9/1977 | Cebrian ................... 514/685 |
| 5,726,314 A | 3/1998 | Powers et al. |
| 6,407,117 B1 | 6/2002 | Bouscarel et al. |
| 6,565,842 B1 | 5/2003 | Sojomihardjo et al. ...... 424/85.1 |
| 6,800,483 B1 | 10/2004 | Danks et al. ................ 435/456 |
| 7,018,631 B1 | 3/2006 | Danks et al. ................ 424/94.6 |
| 7,419,987 B2 * | 9/2008 | Hofgen et al. ............... 514/300 |

FOREIGN PATENT DOCUMENTS

| WO | WO 99/42593 | 8/1999 |
| WO | WO-99/55663 A1 | 11/1999 |

OTHER PUBLICATIONS

Berndt et al. (Journal of the American Chemical Society (1977), 99(25), 8332-4).*
Wadkins et al. Journal med. chem. 2005, 48, 2906-2915.*
Slatter et al. "Bioactivation of the anticancer agent CPT-11 to SN-38 by human hepatic microsomal carboxylesterases and the in vitro assessment of potential drug interactions." Drug Metabolism and Disposition. 1997. vol. 25, No. 10. pp. 1157-1164.
Atsumi et al. "The production of reactive oxygen species by irradiated camphorquinone-related photosensitizers and their effect on cytotoxicity." Archives of Oral Biology. 2001. vol. 46. pp. 391-401.
Wadkins et al. "Identification and Characterization of Novel Benzil (Diphenylethane-1,2-dione) Analogues as Inhibitors of Mammalian Carboxylesterases." Journal of Medicinal Chemistry. 2005. vol. 48, No. 8. pp. 2906-2915.
Joseph Kraut, "Serine Proteases: Structure and Mechanism of Catalysis", Ann. Rev. Biochem. vol. 46, pp. 331-358, 1977.
E.R. Soares, "Identification of a New Allele of *Es-l* Segregating in an Inbred Strain of Mice", Biochemical Genetics, vol. 17, Nos. 7/8, pp. 577-583, 1979.
Akihiko Tanizawa, et al. "Comparison of Topoisomerase I Inhibition, DNA Damage, and Cytotoxicity of Camptothecin Derivatives Presently in Clinical Trials", Journal of the National Cancer Institute, vol. 86, No. 11, pp. 836-841, 1994.
Michael C. Berndt, et al., "Inhibition of Chicken Liver Carboxylesterase by Activated Carbonyls and Carbonyl Hydrates", Biochimica et Biophysica Acta, 1298, pp. 159-166, 1996.
Christopher L. Morton, et al., "Comparison of *Escherichia coli, Saccharomyces cerevisiae, Pichia pastoris, Spodoptera frugiperda*, and COS7 Cells for Recombinant Gene Expression—Application to a Rabbit Liver carboxylesterase", Molecular Biotechnology, vol. 16, pp. 193-202, 2000.
Gialih Lin, et al.; "Quantitative Structure-Activity Relationships for the Pre-Steady-State Inhibition of Cholesterol Esterase by 4-Nitrophenyl-N-substituted Carbamates", Bioorganic & Medicinal Chemistry, vol. 8, pp. 2601-2607, 2000.
Ruchi Khanna, et al., "Proficient Metabolism of Irinotecan by a Human Intestinal Carboxylesterase", Cancer Research, vol. 60, pp. 4725-4728, 2000.
Randy M. Wadkins, et al. Structural Constraints Affect the Metabolism of 7-Ethyl-10-[4-(1-peperidino)-1-piperidino]carbonyloxycamptothecin (CPT-11) by Carboxylesterases, Molecular Pharmacology, vol. 60, No. 2, pp. 355-362, 2001.
Monika Wierdl, et al. "Sensitization of Human Tumor Cells to CPT-11 via Adenoviral-Mediated Delivery of a Rabbit Liver Carboxylesterase", Cancer Research, vol. 61, pp. 5078-5082, Jul. 1, 2001.
P. Bar-On, et al., "Kinetic and Structural Studies on the Interaction of Cholinesterases with the Anti-Alzheimer Drug Rivastigmine", Biochemistry, vol. 41, pp. 3555-3564, 2002.

(Continued)

*Primary Examiner* — Gollamudi Kishore
*Assistant Examiner* — Snigdha Maewall
(74) *Attorney, Agent, or Firm* — Fish & Richardson P.C.

(57) ABSTRACT

This disclosure relates to amides, aryl sulphonamides, aryl ureas, and α,β-diketones derivatives useful as carboxylesterase esterase inhibitors. The disclosure is also directed to the use of these compounds as selective human intestinal carboxylesterase inhibitors and insect carboxylesterase inhibitors. The disclosure is also directed to pharmaceutical compositions and pesticide formulations containing these compounds, and to methods for treating or ameliorating the toxic effects following administration of drugs such as cancer therapy drugs, treating or ameliorating the effects of a drug overdose, and to the use of the compounds for increasing the effectiveness of insecticides and pesticides.

18 Claims, 2 Drawing Sheets

OTHER PUBLICATIONS

Kyoung Jin P. Yoon, et al. Synthesis and Evaluation of Esters and Carbamates to Identify Critical Functional Groups for Esterase-specific Metabolism, Bioorganic & Medicinal Chemistry, vol. 11, pp. 3237-3244, 2003. (Available online Jun. 11, 2003).

Randy M. Wadkins, et al. "Discovery of Novel Selective Inhibitors of Human Intestinal Carboxylesterase for the Amelioration of Irinotecan-Induced Diarrhea: Synthesis, Quantitative Structure-Activity Relationship Analysis, and Biological Activity", Molecular Pharmacology, vol. 56, pp. 1336-1342, 2004.

Berndt et al., 1977, "Ethyl Phenylglyoxylate, a Simultaneous Inhibitor and Substrate of Chicken Liver Carboxylesterase (EC 3.1.1.1). Enzyme-Catalyzed Fragmentation of (E)-Benzil Monoxime O-2,4-Dinitrophenyl Ether", *J. American Chem. Soc.*, 99:8334-5.

* cited by examiner

AMIDE, ARYL SULFONAMIDE, ARYL UREA, AND α,β-DIKETONE DERIVED CARBOXYLESTERASE INHIBITORS, AND THEIR METHODS OF USE

CROSS-REFERENCE TO RELATED APPLICATIONS

This application is a divisional of U.S. application Ser. No. 10/925,367, filed Aug. 24, 2004, which claims priority under 35 U.S.C. §119(e) to U.S. Provisional Application Ser. No. 60/498,778, filed Aug. 29, 2003, which is incorporated by reference herein in its entirety.

REFERENCE TO GOVERNMENT SUPPORT

This invention was made with government support under core grant P30-CA21765 awarded by the National Institutes of Health Cancer Center. The U.S. government may have certain rights in this invention.

FIELD OF THE INVENTION

This invention is directed to the use of amide, aryl sulphonamide, aryl urea, and α,β-diketone compounds as carboxylesterase inhibitors, and particularly to the use of these compounds as selective human intestinal carboxylesterase inhibitors. The compounds are also useful as insect carboxylesterase inhibitors. The invention is also directed to pharmaceutical compositions and pesticide formulations containing the amide, aryl sulphonamide, aryl urea, and α,β-diketone esterase inhibitors, and to methods for treating or ameliorating the toxic effects of drugs, such as cancer therapy drugs, treating or ameliorating the effects of a drug overdose, and to the use of the compounds for increasing the effectiveness of insecticides and pesticides.

BACKGROUND OF THE INVENTION

Carboxylesterase (CE) is one of a sub-class of enzymes known collectively as hydrolases. Hydrolase enzymes catalyze the hydrolysis of various bonds, with carboxylesterase specific for the hydrolysis of both aliphatic and aromatic carboxylic esters, thereby generating an alcohol and a carboxylic acid anion. CEs are ubiquitous serine esterase enzymes that are thought to be involved in the detoxification of xenobiotics, and are found in animal tissues (primarily the liver, serum, lung, kidney, intestine, and blood brain barrier), plants, molds, and yeast. The tissue distribution of these enzymes correlates with their involvement in xenobiotic detoxification.

As yet, no endogenous substrates for CEs have been identified, although they are responsible for the metabolism of many drugs, including CPT-11, cocaine, heroin, meperidine, and capecitabine. These carboxylesterase enzymes are processed in the endoplasmic reticulum of mammalian cells, and hence these proteins can be secreted into the extracellular milieu. Recently, the x-ray crystal structure of a rabbit-liver and a human-liver carboxylesterase have been determined. These studies indicate that the proteins demonstrate similar structures to other esterases including acetylcholinesterases, lipases, etc.

Previously known inhibitors of esterases have included organophosphorous compounds such as di-isopropyl fluorophosphate (DFP), carbamates, piperidine derivatives, and acridine derivatives. These compounds are regarded as highly toxic poisons. The inhibition of chicken liver carboxylesterase by benzil has been reported in a study of the enzymatic mechanism involved. However, the only selective inhibitors of CEs that have been reported are the cyclic organophosphate derivatives, Bomin-1, 2, and 3 (Latoxan, France).

7-ethyl-10-[4-(1-piperidino)-1-piperidino]carbonyloxycamptothecin (Irinotecan, CPT-11) is a widely used anticancer drug that has demonstrated remarkable promise in the treatment of solid tumors. CPT-11 has demonstrated remarkable antitumor activity in both preclinical models and patients with refractory disease and, as such, has recently been approved for the treatment of colon cancer in adults. When administered to patients, CPT-11 is activated by human carboxylesterase to yield its active metabolite, 7-ethyl-10-hydroxycamptothecin (SN-38), which is a potent topoisomerase I poison. Topoisomerases are the enzymes responsible for unwinding and winding chromosomal DNA. In order to allow transcription and translation, DNA must be unwound. SN-38 prevents DNA unwinding, and thus inhibits critical cellular processes in tumor cells, resulting in cell death.

The toxicities associated with this agent include a cholinergic syndrome due to direct inhibition of acetylcholinesterase, and delayed diarrhea due to gastrointestinal toxicity. The gastrointestinal toxicity is thought to occur via two independent mechanisms:

1. SN-38 is conjugated in the liver to yield SN-38 glucuronide (SN-38G). Following deposition into the small intestine via the bile, SN-38G can be cleaved by bacterial glucuronidases to yield the toxic metabolite SN-38, resulting in local irritation and toxicity to the gut.

2. CPT-11 is also eliminated via the bile, and following entry into the gut, CEs present within the intestinal epithelia can convert the drug to SN-38. Hence very high, local concentrations of SN-38 will be produced, resulting in cytotoxicity and hence diarrhea.

The delayed diarrhea associated with CPT-11 administration can be life-threatening and is the dose limiting toxicity for this agent. Potential solutions for ameliorating this toxicity include: (i) the aggressive use of antidiarrheals, such as loperamide and diphenoxylate/atropine, and (ii) the alkalinization of the gut using bicarbonate.

The level of activation of CPT-11 by human plasma in vitro is very low. In contrast, plasma derived from rats and mice is very proficient at CPT-11 activation, with greater than 50% of the drug converted to SN-38 within 1 hour of incubation. Either the levels of the enzymes responsible for CPT-11 metabolism in humans are low, or these human proteins have significantly diverged in structure from their rodent counterparts. Hence, animal models designed to predict tumor responses in humans may overestimate the efficacy of the drug due to the increased plasma activation of CPT-11.

Recently, a rabbit liver carboxylesterase that could efficiently convert CPT-11 to SN-38 was isolated. A human homolog of this carboxylesterase (hCE1) is known. However, expression of hCE1 in human tumor cells does not alter their sensitivity to CPT-11. More recently, it has been demonstrated that both the human and mouse small intestine expresses high levels of carboxylesterases that can convert CPT-11 to SN-38. A cDNA encoding a human small intestinal carboxylesterase (hiCE) has subsequently been identified that is highly efficient at activating CPT-11. Expression of this protein in mammalian cells sensitizes them to the drug.

Therefore, it appears that the activation of CPT-11 in the human intestine by hiCE results in local toxicity, and hence produces the unwanted toxic side effects such as diarrhea. Therefore, before CPT-11 and similar anti-cancer drugs can be utilized to their full potential, there is a need to develop methods for alleviating the toxicity problems associated with administration of these drugs.

There is therefore a need to develop new compounds that are not only useful as general esterase inhibitors, but further, to develop new compounds that are specific for the inhibition of selected carboxylesterases, such as the human small intestine carboxylesterases (hiCEs) that activate drugs such as CPT-11.

The following patents and publications provide relevant background to the present invention. All references cited below are incorporated herein by reference in their entirety and to the same extent as if each reference was individually incorporated by reference. U.S. Pat. Nos. 5,762,314, 6,407,117; Published International Application No. WO 99/42593; Khanna et al., *Cancer Research*, 2000, 60: pp. 4725-4728; Wadkins et al., *Molecular Pharmacology*, 2001, 60(2): pp. 355-362; Wierdl et al., *Cancer Research*, 2001, 61: pp. 5078-5082; Tanizawa et al., *J. Natl. Cancer Inst.*, 1994, 86: pp. 836-42; Morton et al., *Mol. Biotechnol.*, 2000, 16, pp. 193-202; Soares, E. R., *Biochem. Genet.*, 1979, 17, pp. 577-583; and Berndt et al., *Biochimica et Biophysica Acta.*, 1996, 1298, pp. 159-166.

SUMMARY OF THE INVENTION

This invention is directed to the use of amide, aryl sulphonamide, aryl urea, and α,β-diketone compounds as esterase inhibitors.

In one embodiment, these compounds as useful as selective human intestinal carboxylesterase inhibitors.

In a second embodiment, these compounds are useful as insect carboxylesterase inhibitors.

A further embodiment is directed to pharmaceutical compositions containing the amide, aryl sulphonamide, aryl urea, and α,β-diketone esterase inhibitors.

A further embodiment is directed to pesticide formulations containing the amide, aryl sulphonamide, aryl urea, and α,β-diketone esterase inhibitors Further embodiments are directed to a method for treating or ameliorating the toxic effects of drugs (such as the cancer therapy drug CPT-11) administered to a patient, to treating or ameliorating the effects of a drug overdose, and to the use of the compounds for increasing the effectiveness of insecticides and pesticides.

DETAILED DESCRIPTION OF THE INVENTION

Figure 1:
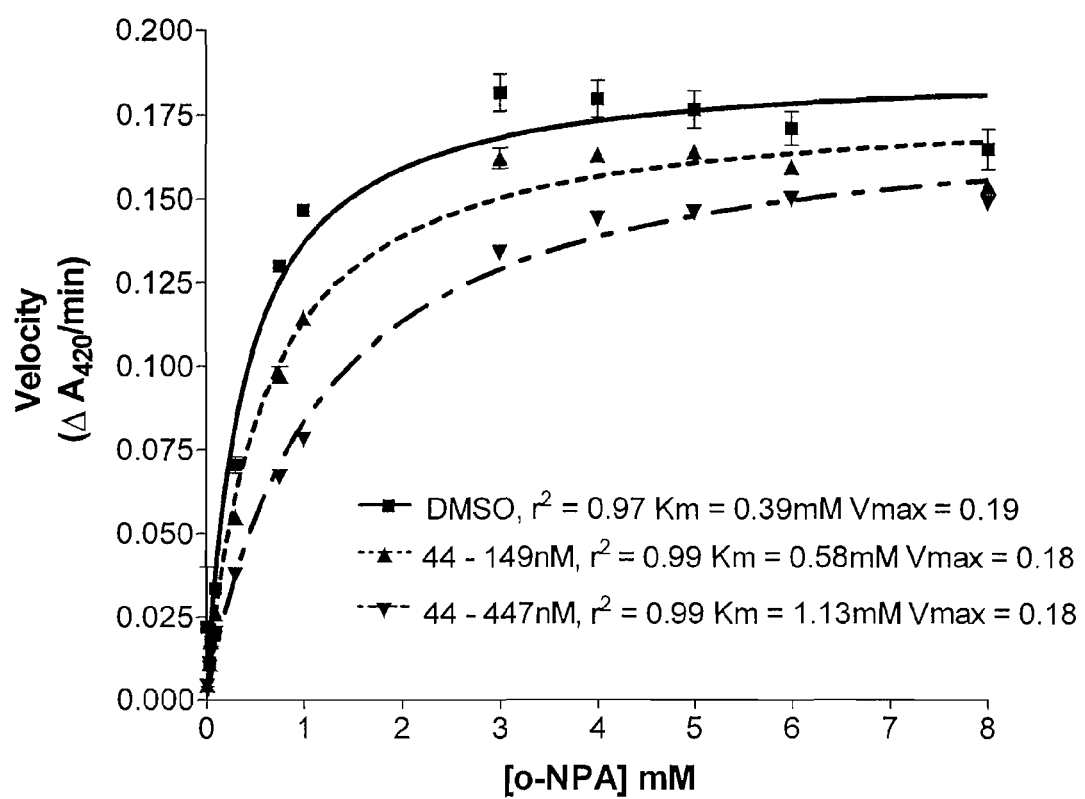
FIG. 1 shows hyperbolic plots of the inhibition of o-NPA metabolism by hiCE using sulphonamide inhibitor 44 at two different concentrations (149 nM and 447 nM).

The present invention is directed to the novel use of amide, aryl sulphonamide, aryl urea, and α,β-diketone derivatives as esterase inhibitors. In one embodiment, the amide, aryl sulphonamide, aryl urea, and α,β-diketone derivatives are useful general carboxylesterase inhibitors. In another embodiment, the amide, aryl sulphonamide, aryl urea, and α,β-diketone derivatives are useful selective carboxylesterase inhibitors. In more specific embodiments, the invention is directed to the use of amide, aryl sulphonamide, aryl urea, and α,β-diketone derivatives as selective human intestinal carboxylesterase (hiCE) inhibitors or selective insect carboxylesterase inhibitors.

The present invention is based, in part, on the discovery that amide, aryl sulfonamide, aryl urea, and α,β-diketone derivatives of Formulas (I)-(V) have esterase inhibitor activity. Previously, these classes of compounds have not been shown to be esterase inhibitors. Furthermore, many of these compounds are useful as selective inhibitors of human intestinal carboxylesterase.

CPT-11 is an anti-cancer drug that is selectively hydrolyzed to SN-38 by a human carboxylesterase. SN-38 is a potent topoisomerase I inhibitor. One of the major problems associated with CPT-11 administration is gastrointestinal toxicity, such as delayed diarrhea, due to activation of CPT-11 by carboxylesterases in the human intestine. By administering the selective hiCE inhibitors of Formula (I)-(V), the conversion of CPT-11 to the active metabolite SN-38 in the gut is minimized, and hence CPT-11-induced gastrointestinal toxicity is ameliorated.

Additionally, these compounds, which do not readily cross cell membranes, are useful as selective inhibitors of other important carboxylesterases, such as insect carboxylesterases.

DEFINITIONS

Unless defined otherwise, all technical and scientific terms used herein generally have the same meaning as commonly understood by one of ordinary skill in the art to which this invention belongs.

The term "pharmaceutically acceptable salts" includes salts of the active compounds which are prepared with relatively nontoxic acids or bases, depending on the particular substituents found on the compounds described herein. Suitable salts include, but are not limited to, organic and inorganic salts, for example, ammonium, acetate salt, citrate salt, halide salt, such as hydrochloride and hydrobromide, hydroxide, sulfate, nitrate, phosphate, perchlorate, tetrafluoroborate, carboxylate, mesylate, fumerate, malonate, succinate, tartrate, acetate, gluconate, and maleate.

The term Aabout@ or Aapproximately@ means within an acceptable error range for the particular value as determined by one of ordinary skill in the art, which will depend in part on how the value is measured or determined, i.e., the limitations of the measurement system. For example, Aabout@ can mean within 1 or more than 1 standard deviations, per the practice in the art. Alternatively, Aabout@ can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The term "esterase inhibiting amount" means an amount of the esterase inhibitor sufficient to inhibit esterase activity by a measurable amount, e.g., by at least 50%, preferably by at least 75%, and more preferably by at least 90%.

The term "gastrointestinal toxicity" means a disorder of the gastrointestinal tract, such as, but not limited to, delayed diarrhea.

The term "alkyl," by itself or as part of another substituent, means, unless otherwise stated, a straight or branched chain radical which may be fully saturated, mono- or polyunsaturated and can include di- and multivalent radicals, having the number of carbon atoms designated (e.g., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, n-pentyl, n-hexyl, n-heptyl, and n-octyl. An unsaturated alkyl group is one having one or more double bonds ("alkenyl") or triple bonds ("alkynyl"). "Alkenyl" refers to a branched or straight chain $C_2$-$C_{24}$ hydrocarbon (for example a $C_2$-$C_{10}$ hydrocarbon, for further example a $C_2$-$C_8$ hydrocarbon, for even further example a $C_2$-$C_6$ hydrocarbon) which can comprise one or more carbon-carbon double bonds. Exemplary alkenyl groups include propylenyl, buten-1-yl, isobutenyl, penten-1-yl, 2,2-methylbuten-1-yl, 3-methylbuten-1-yl, hexan-1-yl, hepten-1-yl, octen-1-yl, and the like. "Alkynyl" refers to an unsaturated acyclic $C_2$-$C_{24}$ hydrocarbon for example a $C_2$-$C_{10}$ hydrocarbon, for further example a $C_2$-$C_8$ hydrocarbon, for even further example a $C_2$-$C_6$ hydrocarbon) which can comprise one or more carbon-carbon triple bonds. Exemplary alkynyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl, 3,3-dimethyl-butyn-1-yl, and the like. Typically, an alkyl, alkenyl, or alkynyl group having 6 or fewer carbon atoms is referred to as "lower alkyl", "lower alkenyl", or "lower alkynyl", respectively.

Cycloalkyl means a saturated or unsaturated cyclic hydrocarbon radical, such as, but not limited to, cyclopropyl, cyclobutyl, cyclopentyl, cyclohexyl, cyclohexenyl, cyclohepta-1,3-dienyl, cyclooctadienyl, (cyclohexyl)methyl, and cyclopropylmethyl.

Heterocycloalkyl means a cycloalkyl radical possessing one or more heteroatoms selected from N, O, and S, wherein the nitrogen, carbon and sulfur atoms are optionally oxidized, and the nitrogen atom(s) are optionally quaternized. Additionally, for heterocycloalkyl, a heteroatom can occupy the position at which the heterocycle is attached to the remainder of the molecule. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, furan-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom.

The term "aryl" means, unless otherwise stated, a substituted or unsubstituted polyunsaturated, aromatic, hydrocarbon substituent which can be a single ring or multiple rings (preferably from 1 to 3 rings), which are fused together or linked covalently. The term "heteroaryl" refers to a category of aryl groups (or rings) that contain from one to four heteroatoms selected from N, O, and S, wherein the nitrogen, carbon and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. "Aryl", including "heteroaryl", also encompass ring systems in which one or more non-aromatic ring systems are fused, or otherwise bound, to an aryl or heteroaryl system.

Each of the above terms (e.g., "alkyl," "cycloalkyl," "aryl" and "heteroaryl") include both substituted and unsubstituted forms of the indicated radical. Preferred substituents for each type of radical are provided below.

Substituents for the alkyl, and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generally referred to as "alkyl substituents" and "heteroalkyl substituents," respectively, and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR"R', —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, the aryl substituents and heteroaryl substituents are generally referred to as "aryl substituents" and "heteroaryl substituents," respectively and are varied and selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R")=NR'", —S(O)R', —S(O)$_2$R', —S(O)$_2$NR"R', —NRSO$_2$R', —CN, —NO$_2$, —R', —N3, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl. When a compound of the invention includes more than one R group, for example, each of the R groups is independently selected as are each R', R", R'" and R"" groups when more than one of these groups is present.

As used herein, the term "heteroatom" includes oxygen (O), nitrogen (N), sulfur (S) and silicon (Si).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocyclic groups.

Esterase Inhibitor Compounds

Amide compounds that have been found to be esterase inhibitors are of Formula (I) and (II):

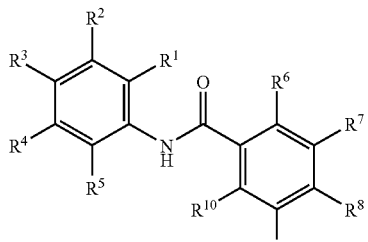

(I)

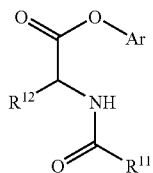

(II)

wherein $R^1$ to $R^{12}$ are each independently hydrogen, $C_1$-$C_6$ linear or branched alkyl, substituted alkyl, aryl, substituted aryl, heteroaryl, substituted heteroaryl, hydroxyl, halogen, or $C_1$-$C_6$ alkoxy; and Ar is phenyl, substituted phenyl, naphthyl or substituted naphthyl. Optionally, $R^8$ and $R^9$ may be linked to form a substituted or unsubstituted aryl or heteroaryl ring system.

In one embodiment of the compound of Formula (I), at least one of $R^1$ to $R^5$ is chlorine and $R^6$ is hydroxyl. In a specific embodiment of the compound of Formula (II), Ar is naphthyl, $R^{11}$ is phenyl, and $R^{12}$ is benzyl. In a second specific embodiment of the compound of Formula (II), Ar is naphthyl, $R^{11}$ is methyl, and $R^{12}$ is isopropyl. In a third specific embodiment of the compound of Formula (II), Ar is naphthyl, $R^{11}$ is methyl, and $R^{12}$ is isobutyl.

Aryl sulphonamide compounds that have been found to be esterase inhibitors are of formula (III):

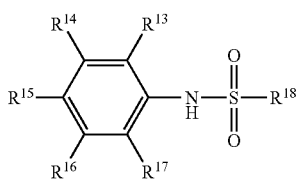

(III)

wherein $R^{13}$, $R^{14}$, $R^{16}$ and $R^{17}$ are each independently hydrogen, halogen, $C_1$-$C_6$ linear or branched alkyl, or $R^{16}$ and $R^{17}$ may optionally be linked to form an aryl or heteroaryl ring system; $R^{15}$ is hydrogen, $C_1$-$C_6$ alkoxy, optionally substituted phenoxy, or $NHSO_2R^{19}$; wherein $R^{19}$ is $C_1$-$C_6$ linear or branched alkyl, phenyl, mono-, di- or tri-halosubstituted phenyl or $S_2C_6H_5NHSO_2CH_3$; and $R^{18}$ is hydrogen, $C_1$-$C_6$ linear or branched alkyl, halogen, phenyl, halosubstituted phenyl or $[C_6H_2(CH_3)_2]SO_2NHC_6H_5$.

Aryl urea compounds that have been found to be to be esterase inhibitors are of formula (IV):

(IV)

wherein $R^{20}$ to $R^{29}$ are each independently hydrogen, halogen, $C_1$-$C_6$ linear or branched alkyl or $NO_2$. In one embodiment, $R^{22}$ or $R^{27}$ is $NO_2$.

α,β-diketone compounds that have been found to be to be esterase inhibitors are of formula (V):

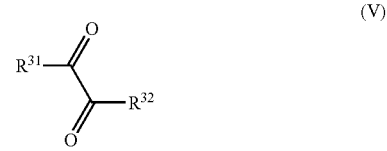

(V)

wherein $R^{31}$ and $R^{32}$ are each independently aryl or heteroaryl, optionally substituted with one or more hydrogen, halogen, hydroxy, $C_1$-$C_6$ linear or branched alkyl, $C_1$-$C_6$ linear or branched halo-alkyl, $C_1$-$C_6$ alkoxy, $NR_{33}R_{34}$, COOH, or $NO_2$, wherein $R_{33}$ and $R_{34}$ are independently hydrogen or $C_1$-$C_6$ linear or branched alkyl.

$R^{31}$ and $R^{32}$ may include, but are not limited to, phenyl, pyridyl, furanyl, thienyl, and substituted derivatives thereof. Alternatively, $R^{31}$ and $R^{32}$ may be linked to form an optionally substituted polycyclic aryl or heteroaryl ring system. In one embodiment of the compound of Formula (V), when $R^{31}$ is unsubstituted phenyl, $R^{32}$ is not unsubstituted phenyl (i.e., $R^{31}$ and $R^{32}$ are not both unsubstituted phenyl).

Examples of α,β-diketone compounds useful as esterase inhibitors include, but are not limited to, benzil, furil, thenil, pyridil, aceanthrenequinone, 9,10-phenanthrenequinone, acenaphthenequinone, 1,2,-naphthoquinone, and substituted derivatives thereof.

Additionally, since the structures of these compounds are novel with respect to their ability to inhibit mammalian esterases, certain esterase inhibitors of Formulae (I)-(V), or derivatives thereof, are useful as selective inhibitors of specific mammalian carboxylesterases. Hence inhibitors with these core structures with selectivity toward other classes of carboxylesterases are provided.

Many amide, aryl sulfonamide, aryl urea, and α,β-diketone compounds falling into the foregoing classes are available from commercial sources, including Sigma Aldrich (St. Louis, Mo.), ChemDiv (San Diego, Calif.), Asinex (Moscow, Russia), and Maybridge (Cornwall, U.K.) The commercially available compounds can be readily modified by routine synthetic methods to generate derivative compounds.

Alternatively, any compound for use in the present invention can be generated synthetically, by standard organic synthetic methods readily known to one of ordinary skill in the art, e.g., as set forth below.

Preparation of Compounds of Formulas (I) and (II)

Numerous synthetic methods are known to the art to form amides (see "Comprehensive Organic Transformations", Chapter 9, Larock, R. C. 1989, VCH Publishers, New York). Compounds of Formulas (I) and (II) may be prepared in a similar manner to that outlined below for the preparation of compound 42.

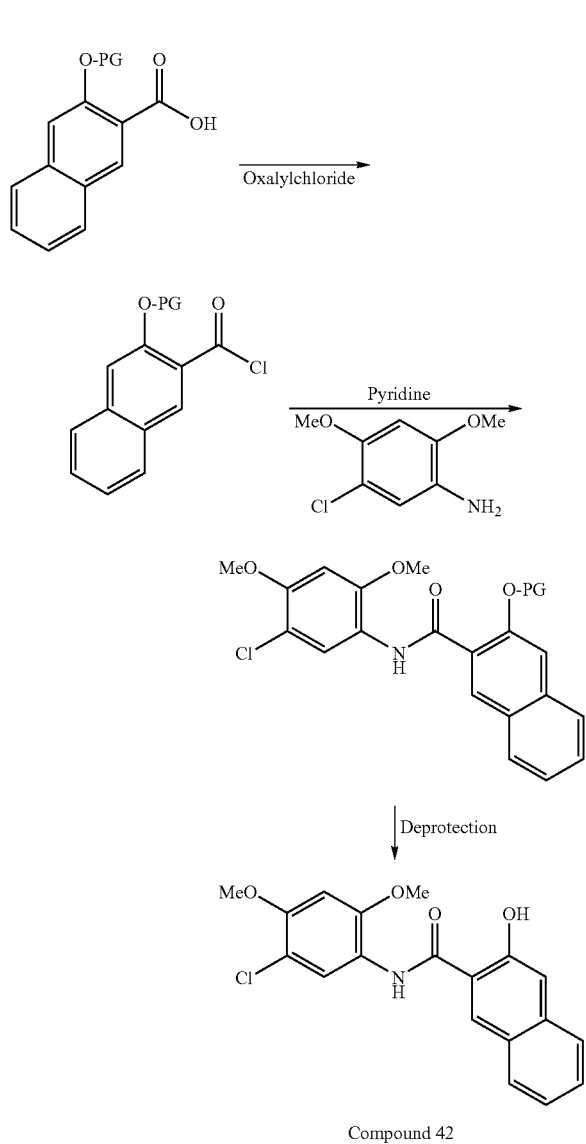

Compound 42

A protected naphthoic acid (PG=protecting group, see "Protective Groups in Organic Synthesis", 2$^{nd}$ Ed, Greene and Wuts, 1991, Wiley, New York) is converted to the acyl-chloride using oxalylchloride. The acid chloride is directly converted to the amide by addition of the appropriate aniline dissolved in pyridine. Deprotection of the alcohol followed by isolation and purification affords Compound 42.

Preparation of Compounds of Formula (III)

Methods to prepare aryl and alkyl sulphonamides are well known to the art (see "Advanced Organic Chemistry", 4$^{th}$ ed, pp 496-498, March, J., 1992, Wiley, New York). Compounds of Formula (III) may be prepared in a similar manner to that outlined below for the preparation of compound 50.

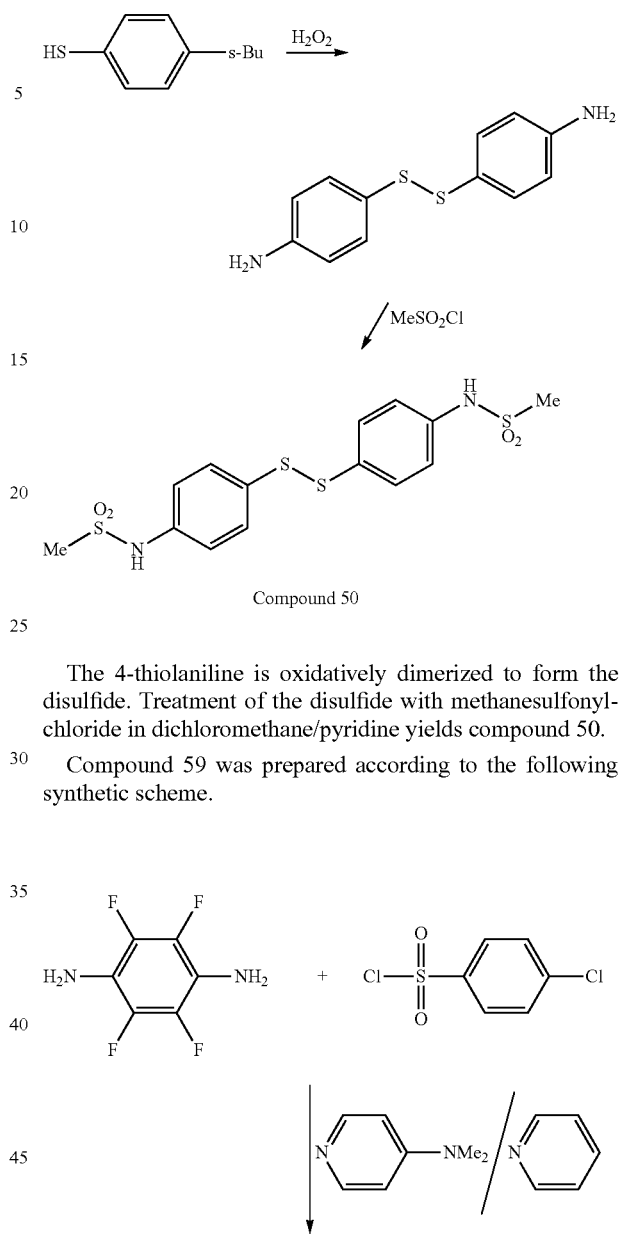

Compound 50

The 4-thiolaniline is oxidatively dimerized to form the disulfide. Treatment of the disulfide with methanesulfonyl-chloride in dichloromethane/pyridine yields compound 50.

Compound 59 was prepared according to the following synthetic scheme.

Compound 59

Preparation of Compounds of Formula (Iv)

Ureas and their preparation are well know to one skilled in the art (see "Introduction to Organic Chemistry", 2$^{nd}$ ed., pp. 785-786, Streitweiser and Heathcock, 1981, MacMillan New York). Diaryl ureas may be prepared in a similar manner to that outlined below for the preparation of compound 53.

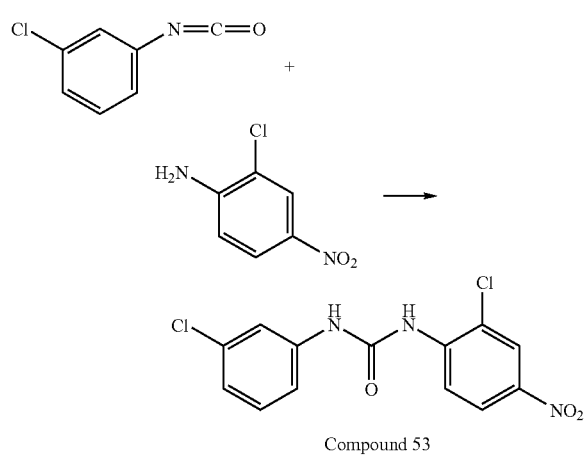

Compound 53

The diaryl urea is directly formed by the reaction of an isocyanate and the appropriate amine.

Preparation of Compounds of Formula (V)

Two potential synthetic schemes are possible for the preparation of α,β-diketone compounds of Formula (V). For benzil, and derivatives thereof, the first uses the condensation of the substituted benzaldehyde in the presence of NaOH and thiamine to yield the benzoin derivative. Oxidation of the benzoin derivative in the presence of $Cu^{2+}$, acetic acid, and ammonium nitrate, or concentrated nitric acid, produces the benzil compound of Formula (V) virtually quantitative yield. This is shown below for compound 17.

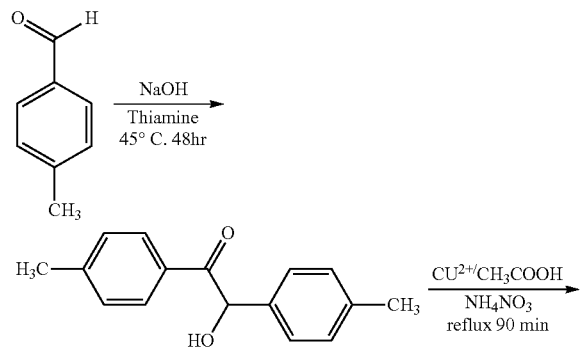

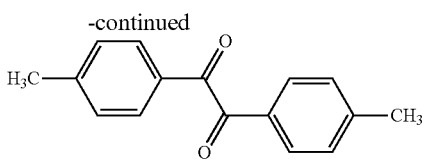

An alternate synthetic scheme for the preparation of benzil compounds of Formula (V) involves the use of trimethylsilyl cyanide. Following reaction of the substituted benzaldehyde with trimethylsilyl cyanide in the presence of a zinc iodide catalyst, the cyanohydrin derivative thus formed is reacted with the substituted benzoyl acid chloride to yield the benzil compound of Formula (V).

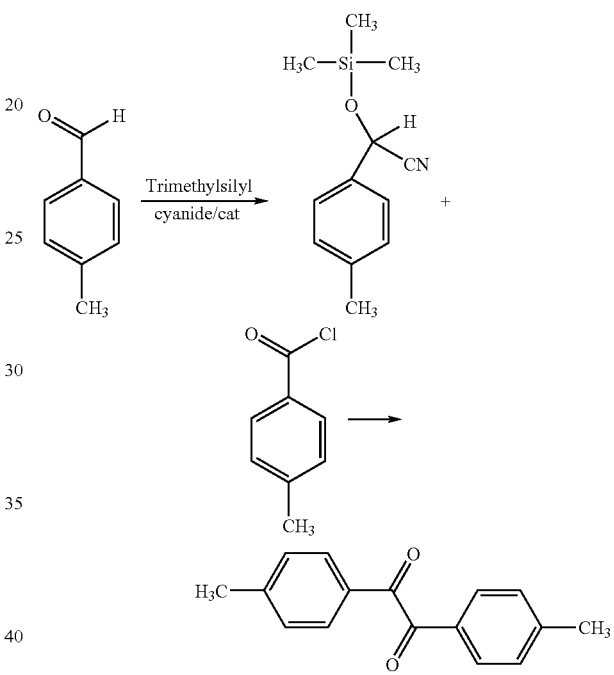

Thenil, pyridil, and furil analogs may be prepared in a similar manner to that given above, using thiophenecarboxyaldehyde, pyridinecarboxaldehyde, and furaldehyde, or substituted derivatives thereof, as the starting material, respectively.

Suitable, but non limiting, examples of α,β-diketone derivatives useful as carboxylesterase inhibitors in the present invention are set forth in Table 1.

TABLE 1

α,β-Diketone Derivatives Useful as Carboxylesterase Inhibitors

| Chemical Structure | Name of Compound | Compound Code |
|---|---|---|
| 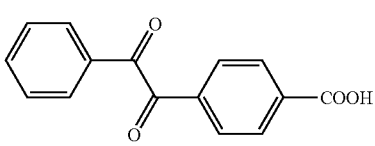 | 4-[oxo(phenyl)acetyl]benzoic acid | 1 |

TABLE 1-continued

α,β-Diketone Derivatives Useful as Carboxylesterase Inhibitors

| Chemical Structure | Name of Compound | Compound Code |
|---|---|---|
| 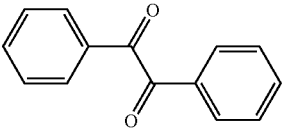 | Benzil Diphenylethane-1,2-dione | 2 |
| 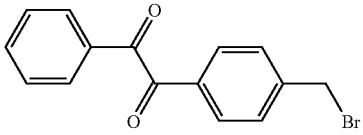 | 1-[4-bromomethyl)phenyl]-2-phenylethane-1,2-dione | 3 |
| 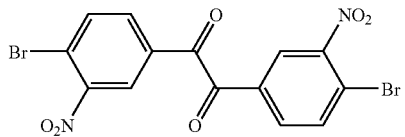 | 1,2-bis(4-bromo-3-nitrophenyl)ethane-1,2-dione | 4 |
| 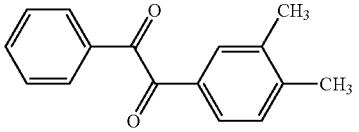 | 1-(3,4-dimethylphenyl)-2-phenylethane-1,2-dione | 5 |
| 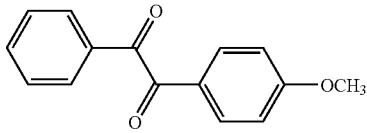 | 1-(4-methoxyphenyl)-2-2phenylethane-1,2-dione | 6 |
| 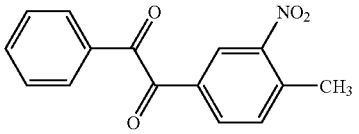 | 1-(4-methyl-3-nitrophenyl)-2-phenylethane-1,2-dione | 7 |
| 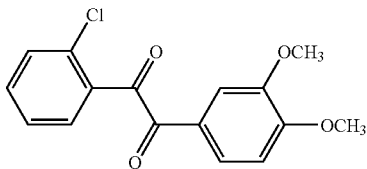 | 1-(2-chlorophenyl)-2-(3,4-dimethoxyphenyl)ethane-1,2-dione | 8 |
| 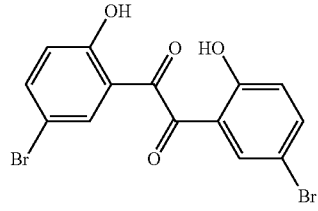 | 1,2-bis(5-bromo-2-hydroxyphenyl)ethane-1,2-dione | 9 |
| 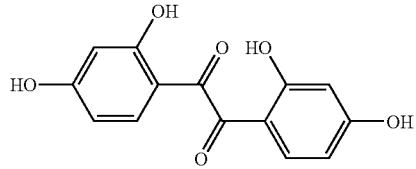 | 1,2-bis(2,4-dihydroxyphenyl)ethane-1,2-dione | 10 |

TABLE 1-continued

α,β-Diketone Derivatives Useful as Carboxylesterase Inhibitors

| Chemical Structure | Name of Compound | Compound Code |
|---|---|---|
| 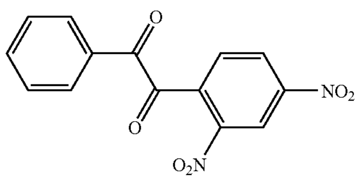 | 1-(2,4-dinitrophenyl)-2-phenylethane-1,2-dione | 11 |
| 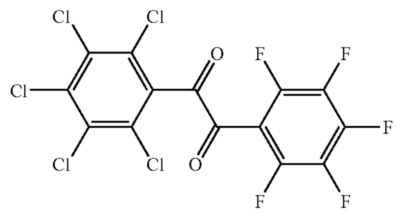 | 1-(pentachlorophenyl)-2-(pentafluorophenyl)ethane-1,2-dione | 12 |
| 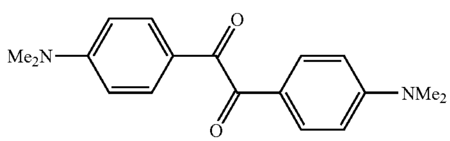 | 1,2-bis[4(dimethylamino)phenyl]ethane-1,2-dione | 13 |
| 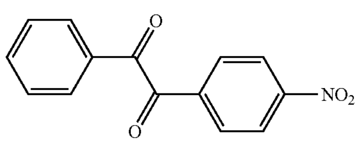 | 1-(4-nitrophenyl)-2-phenylethane-1,2-dione | 14 |
| 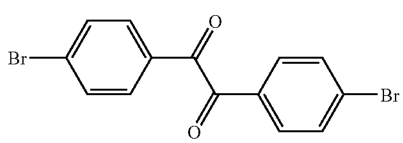 | 4,4' dibromobenzil ((1,2-bis(4-bromophenyl)ethane-1,2-dione) | 15 |
| 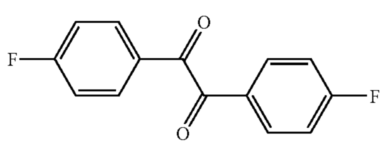 | 4-4' difluorobenzil (1,2-bis(4-fluorophenyl)ethane-1,2-dione) | 16 |
| 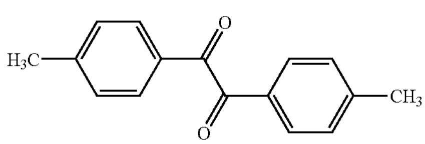 | 1,2-bis(4-methylphenyl)ethane-1,2-dione | 17 |
| 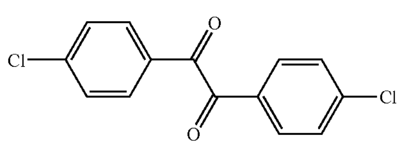 | 4-4' dichlorobenzil 1,2-bis(4-chlorophenyl)ethane-1,2-dione | 18 |
| 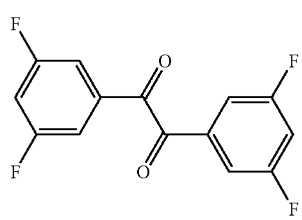 | 1,2-bis(3,5-difluorophenyl)ethane-1,2-dione | 19 |

TABLE 1-continued

α,β-Diketone Derivatives Useful as Carboxylesterase Inhibitors

| Chemical Structure | Name of Compound | Compound Code |
|---|---|---|
| 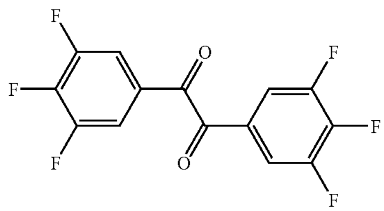 | 1,2-bis(3,4,5-trifluorophenyl)ethane-1,2-dione | 20 |
| 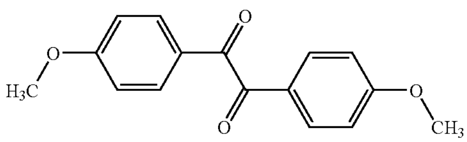 | 1,2-bis(4-methoxyphenyl)ethane-1,2-dione | 21 |
| 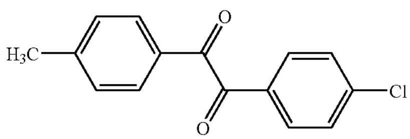 | 1-(4-chlorophenyl)-2-(4-methylphenyl)ethane-1,2-dione | 22 |
| 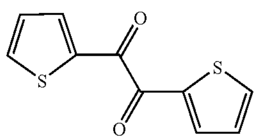 | Thenil<br>1,2-dithien-2-yl-ethane-1,2-dione | 23 |
| 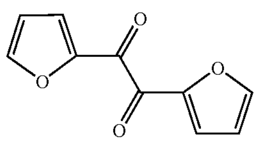 | Furil<br>1,2-di-2-furylethane-1,2-dione | 24 |
| 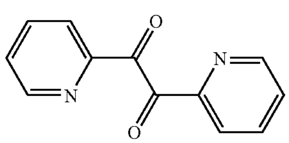 | Pyridil<br>1,2-dipyridin-2-ylethane-1,2-dione | 25 |
| 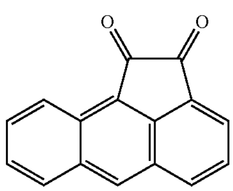 | Aceanthrenequinone<br>Aceanthrylene-1,2-dione | 26 |
| 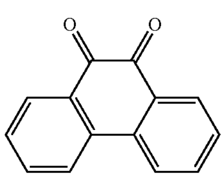 | 9,10-Phenanthrenequinone<br>Phenanthrene-9,10-dione | 27 |
| 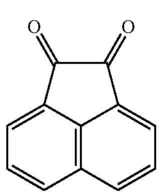 | Acenaphthenequinone<br>Acenaphthylene-1,2-dione | 28 |

TABLE 1-continued

α,β-Diketone Derivatives Useful as Carboxylesterase Inhibitors

| Chemical Structure | Name of Compound | Compound Code |
|---|---|---|
|  | 1,2-Napthoquinone<br>Naphthalene-1,2-dione | 29 |
|  | 2-2' dichlorobenzil<br>1,2-bis(2-chlorophenyl)ethane-1,2-dione | 30 |
| 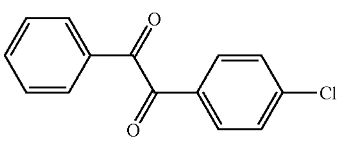 | 1-(4-chlorophenyl)-2-phenylethane-1,2-dione | 31 |
| 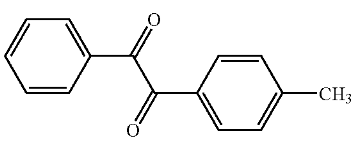 | 1-(4-methylphenyl)-2-phenylethane-1,2-dione | 32 |
| 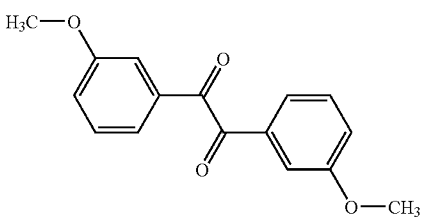 | 1,2-bis(3-methoxyphenyl)ethane-1,2-dione | 33 |
| 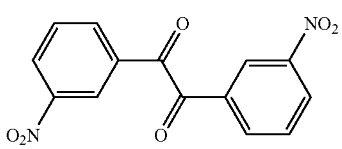 | 1,2-bis(3-nitrophenyl)ethane-1,2-dione | 34 |
| 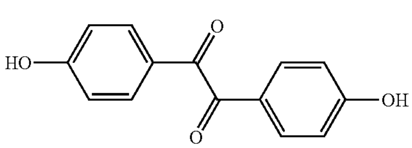 | 1,2-bis(4-hydroxyphenyl)ethane-1,2-dione | 35 |
| 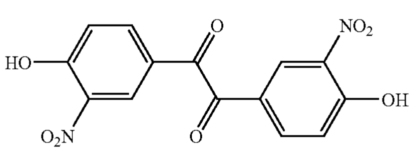 | 1,2-bis(4-hydroxy-3-nitrophenyl)ethane-1,2-dione | 36 |
| 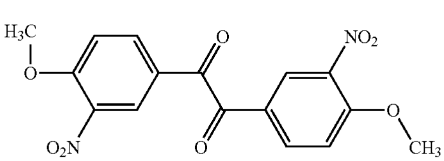 | 1,2-bis(4-methoxy-3-nitrophenyl)ethane-1,2-dione | 37 |

TABLE 1-continued

α,β-Diketone Derivatives Useful as Carboxylesterase Inhibitors

| Chemical Structure | Name of Compound | Compound Code |
|---|---|---|
| 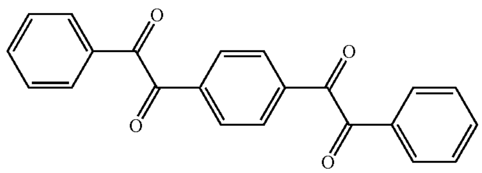 | Bisbenzil 1-{4-[oxo(phenyl)acetyl]phenyl}-2-phenylethane-1,2-dione | 38 |

Compounds 26-29, and 33 are commercially available from Sigma Aldrich (St. Louis, Mo.) Compound 30 is commercially available from VWR/Lancaster (Swedesboro, N.J.). Compound 31 is commercially available from Alfa Aesa (Ward Hill, Mass.). Compound 32 is commercially available from Toronto Research Chemicals (Toronto, Canada). Compounds 34-37 are commercially available from Industrial Research Limited (Auckland, New Zealand). Compound 38 is commercially available from TCI America (Portland, Oreg.).

Uses of the Esterase Inhibitors

General Inhibition of Carboxylesterases

One embodiment of the present invention is the use of amide, aryl sulphonamide, aryl urea, and benzil compounds of Formulas (I)-(V), or derivatives thereof, as general carboxylesterase inhibitors. Specific, but none limiting, examples of the compounds of Formula (V) that have been found to be general carboxylesterase inhibitors include compounds 1, 2, 3, 5, 6, 7, 14, 16, 17, 19, 20, 22, and 23.

In addition, other compounds that have been found to be general carboxylesterase inhibitors are set forth in Table 2.

TABLE 2

General carboxylesterase Inhibitors

| Chemical Structure | Class and Name of Compound | Compound Code |
|---|---|---|
| 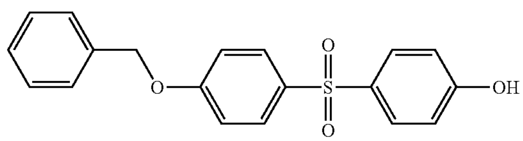 | Sulfone 4-{[4-(benzyloxy)phenyl]sulfonyl}phenol | 39 |
| 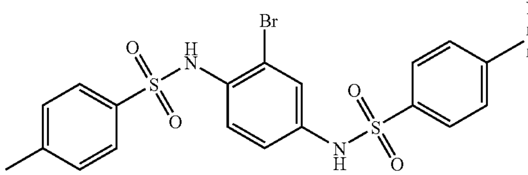 | Sulfonamide N-(2-bromo-4{[4-methylphenyl)sulfonyl]amino}phenyl)-4-methylbenzenesulfonamide | 40 |
| 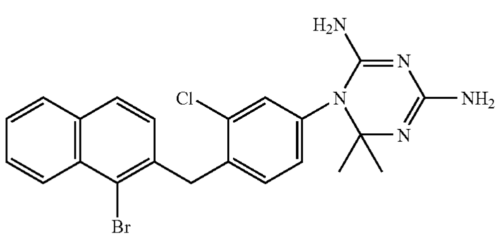 | Triazene 1-{4-[(1-bromo-2-naphthyl)methyl]-3-chlorophenyl}-6,6-dimethyl-1,6-dihydro-1,3,5-triazine-2,4-diamine | 41 |

Inhibition of Human Intestinal Carboxylesterase (hiCE)

A further embodiment of the present invention is the use of amide, aryl sulphonamide aryl urea, and α,β-diketone compounds of Formulas (I)-(V), or derivatives thereof, as selective human intestinal carboxylesterase (hiCE) inhibitors. Specific, but non-limiting, examples of the compounds of Formulas (I)-(V) that have been found to be selective inhibitors of human small intestinal carboxylesterase are given in Table 3.

TABLE 3

Structures of Selective Human Small Intestinal Carboxylesterase Inhibitors

| Chemical Structure | Class and Name of Compound | Compound Code |
|---|---|---|
| 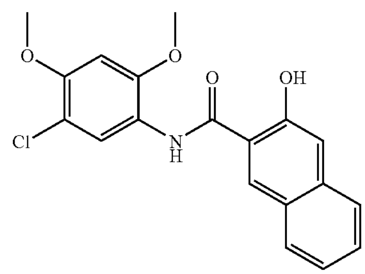 | Amide<br>N-(5-chloro-2,4-dimethoxyphenyl)-3-hydroxy-2-naphthamide | 42 |
| 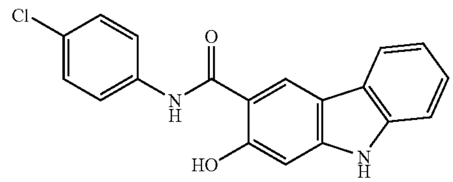 | Amide<br>N-(4-chlorophenyl)-8-hydroxy-4aH-carbazole-7-carboxamide | 43 |
| 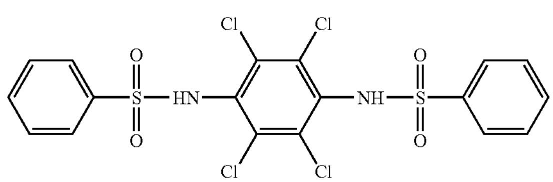 | Sulphonamide<br>N-{2,3,5,6-tetrachloro-4-[(phenylsulfonyl)amino]phenyl}benzenesulfonamide | 44 |
| 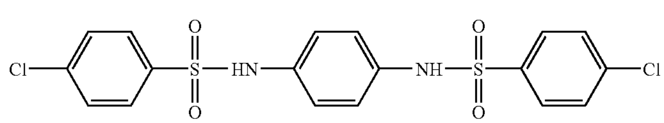 | Sulphonamide<br>4-chloro-N-(4-{[(4-chlorophenyl)sulfonyl]amino}phenyl)benzenesulfonamide | 45 |
| 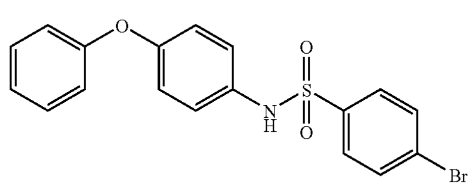 | Sulphonamide<br>4-bromo-N-(4-phenoxyphenyl)benzenesulfonamide | 46 |
| 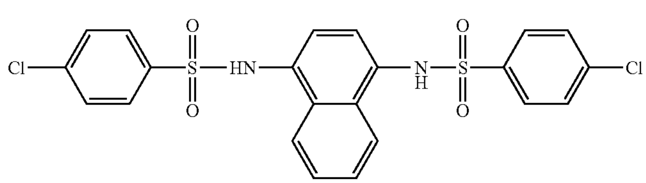 | Sulphonamide<br>4-chloro-N-(4-{[(4-chlorophenyl)sulfonyl]amino}-1-naphthyl)benzenesulfonamide | 47 |
| 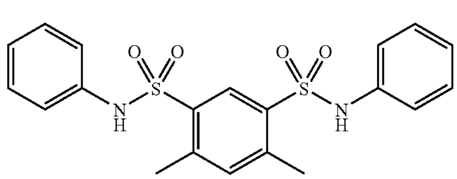 | Sulphonamide<br>4,6-dimethyl-N,N'-diphenylbenzene-1,3-disulfonamide | 48 |
| 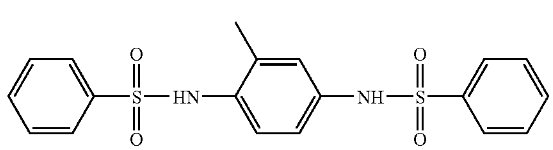 | Sulphonamide<br>N-{2-methyl-4-[(phenylsulfonyl)amino]phenyl}benzenesulfonamide | 49 |

TABLE 3-continued

Structures of Selective Human Small Intestinal Carboxylesterase Inhibitors

| Chemical Structure | Class and Name of Compound | Compound Code |
|---|---|---|
| | Sulphonamide<br>N-[4-({4-[(methylsulfonyl)amino]phenyl}dithio)phenyl]methanesulfonamide | 50 |
| | Sulphonamide<br>N-{4-[(phenylsulfonyl)amino]phenyl}benzenesulfonamide | 51 |
| | Sulphonamide<br>4-chloro-N-(4-ethoxyphenyl)benzenesulfonamide | 52 |
| | Urea<br>N-(2-chloro-4-nitrophenyl)-N'-(4-chlorophenyl)urea | 53 |
| | Urea<br>N-(2,6-dimethylphenyl)-N'-(4-nitrophenyl)urea | 54 |
| | Urea<br>N-(3-fluorophenyl)-N'-(2-methyl-4-nitrophenyl)urea | 55 |
| | Urea<br>N-(2-methyl-4-nitrophenyl)-N'-phenylurea | 56 |
| | Amide<br>2-Benzoylamino-3-phenyl-propionic acid naphthalene-2-yl ester | 57 |

TABLE 3-continued

Structures of Selective Human Small Intestinal Carboxylesterase Inhibitors

| Chemical Structure | Class and Name of Compound | Compound Code |
|---|---|---|
| [structure] | Amide<br>2-naphthyl 2-(acetylamino)-4-methylpentanoate | 58 |
| [structure] | Sulfonamide<br>4-chloro-N-(4{[(4-chlorophenyl)sulfonyl]amino}2,3,4,6-tetrafluorophenyl) benzenesulfonamide | 59 |

The compounds identified in Table 3 were obtained from the following sources, as shown in Table 4:

TABLE 4

Commercial Sources of the Compounds Identified in Table 3

| Compound Code | Source | Catalog # | Alternate Source | Catalog # |
|---|---|---|---|---|
| 42 | ChemDiv | 1125-0434 | Asinex | BAS 3819227 |
| 43 | ChemDiv | 000A-0340 | Asinex | BAS 1057195 |
| 44 | Asinex | BAS 0126340 | | |
| 45 | ChemDiv | 0896-7238 | Asinex | BAS 0126335 |
| 46 | ChemDiv | 4049-0210 | ChemDiv | 3365-0568 |
| 47 | Asinex | BAS 0459805 | | |
| 48 | ChemDiv | 0262-0298 | Asinex | BAS 0116665 |
| 49 | Sigma Aldrich | S739391 | | |
| 50 | Synthesis | described | herein | |
| 51 | ChemDiv | 0896-7239 | | |
| 52 | ChemDiv | 4063-0024 | Asinex | BAS 1358536 |
| 53 | Sigma Aldrich | S607258 | | |
| 54 | Sigma Aldrich | S713805 | | |
| 55 | Sigma Aldrich | S844829 | | |
| 56 | Sigma Aldrich | S610461 | | |
| 57 | Sigma Aldrich | S44975 | | |
| 58 | Sigma Aldrich | S776955 | | |
| 59 | Synthesis | described | herein | |

Inhibition of acetylcholinesterase (AcChE) would be an undesirable property of the compounds of the selective human intestinal carboxylesterase inhibitors identified in Table 3, and make their use clinically impractical. Since AcChE is the target of many nerve gases, compounds that inhibit this enzyme would be highly toxic and would have very little use in humans. None of the selective carboxylesterases identified in Table 3 were found to inhibit AcChE.

The selective human intestinal carboxylesterase inhibitors identified in Table 3 have been found not to cross cell membranes, i.e., not to inhibit carboxylesterase activity intracellularly. Thus the compounds identified in Table 3 cannot easily translocate from the intestine to the bloodstream.

Figure 2:
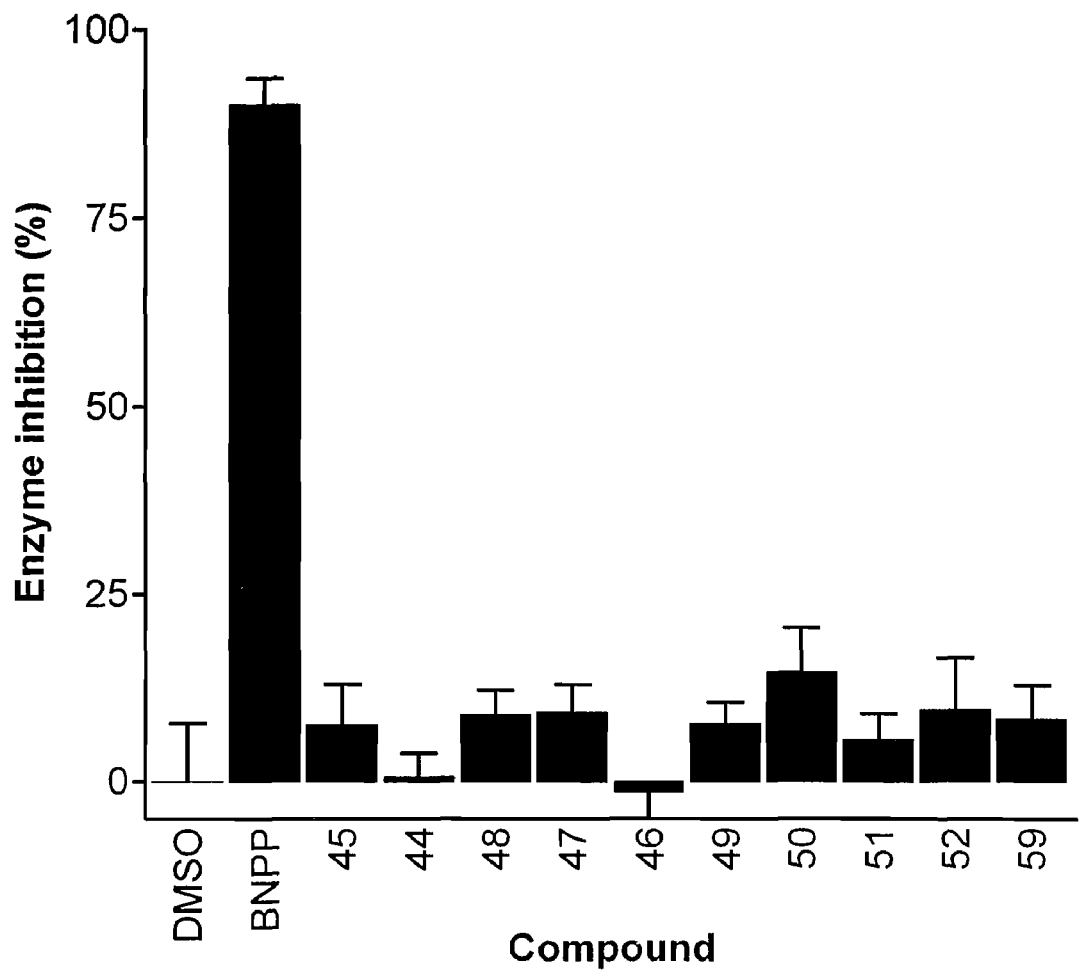
FIG. 2 shows the carboxylesterase activity in enzyme preparations after preincubation with sulphonamide inhibitors 44-52 and 59.

The sulphonamide human intestinal carboxylesterase inhibitors identified in Table 3 have also been found to be partially competitive inhibitors of hiCE, and to inhibit hiCE in a reversible manner. As seen in FIG. 1, when hiCE is incubated in the presence of 149 nM or 447 nM of compound 44, (N-{2,3,5,6-tetrachloro-4-[(phenylsulfonyl)amino]phenyl} benzene sulfonamide), no change in the apparent Vmax (the velocity of the enzyme at infinite substrate concentration) is observed, but an increase in the Km values for hiCE occurs from 0.391 nM to 0.584 nM and 1.132 nM, respectively. FIG. 2 demonstrates that the sulfonamide inhibitors 44-52 and 59 do not result in irreversible inhibition of hiCE. After incubation with either 10 μM of the compounds, or a concentration equivalent to five times the Ki value, for 1 hour on ice, residual carboxylesterase activity was determined. Bis-(4-nitrophenyl) phosphine (BNPP), an irreversible esterase inhibitor, was used as a control. Since the enzyme and inhibitor were diluted at least 250-fold in the CE assay, loss of activity can only occur from direct inactivation of the protein by the sulfonamide analog during the preincubation period. As can be seen from FIG. 2, none of the sulfonamide compounds resulted in irreversible inhibition of the hiCE protein.

Inhibition of Insect Carboxylesterases

Insects detoxify pesticides with carboxylesterases, and insecticide resistance to pesticide compounds can occur via a single acid point mutation in the carboxylesterase protein that renders the enzyme more efficient at detoxification. Development of pesticide resistance can lead to ineffective pesticide application and widespread crop damage, or in the case of mosquitoes carrying diseases like West Nile virus, public health threats. The development of pesticide resistance may result in heavier application of pesticides, which can harm the environment, including fish and animals, and ultimately harm people, particularly due to pesticide residues in foods. Therefore, a further embodiment of the present invention is the use of the amide, aryl sulphonamide, aryl urea, and α,β-diketone compounds of Formulas (I)-(V), or derivatives thereof, as selective insect carboxylesterase inhibitors, thereby allowing for an increase in the efficacy of currently available pesticides. Formulations comprising a compound active as a pesticide and an amide, aryl sulphonamide, aryl urea, or α,β-diketone insect carboxylesterase inhibitor of Formulas (I)-(V), or derivatives thereof, or combinations thereof, are also envisaged. Suitable compounds active as pesticides include, but are not limited to, malathion, parathion, pirimicarb, and chlorpyrifos.

Modulation of Drug Metabolism

In a further embodiment of the present invention, amide, aryl sulphonamide, aryl urea, and α,β-diketone compounds of Formulas (I)-(V), or derivatives thereof, can be used to modulate drug and metabolite levels in humans. Carboxylesterases are involved in the metabolism of a wide variety of drugs in the human body, including, but not limited to, cocaine, heroin, meperidine, capecitabine and flumazenil. Therefore, the esterase inhibitors of Formulas (I)-(V) identified in the present invention may be used to modulate drug and metabolite levels in the human body. One embodiment is the use of amide, aryl sulphonamide, aryl urea, and α,β-diketone compounds for the amelioration of toxicity following a drug overdose in a human patient. Specifically, the compounds of Formulas (I)-(V) may be used to prevent drug metabolism and prove useful in the treatment of individuals who have overdosed on drugs such as, but not limited to, cocaine and/or heroin.

Therapeutic Compositions and Regimens

According to the present invention, a therapeutic compound can be formulated in a pharmaceutical composition of the invention to be introduced parenterally, transmucosally, e.g., orally, nasally, or rectally, or transdermally. Parenteral administration includes, but is not limited to, intravenous, intra-arteriole, intramuscular, intradermal, subcutaneous, intraperitoneal, intraventricular, and intracranial administration, e.g., by injection.

When formulated in a pharmaceutical composition, a therapeutic compound can be admixed with a pharmaceutically acceptable carrier or excipient. The phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

A preferred mode of administration of the specific inhibitors of the human intestinal carboxylesterase, identified in Table 1, is oral administration. When administered orally, these poorly bioavailable molecules are expected to either remain in the gut or only enter the epithelia of the lining of the intestine, and hence inactivate any carboxylesterase in these tissues, thus preventing subsequent activation of CPT-11 that is deposited in the duodenum from the bile.

A preferred mode of administration of the esterase inhibits of Formula (I)-(V), for the inhibition of drug metabolism in the blood stream or highly perfused organs like the liver, is intravenous administration. This should lead to complete inhibition of CE activity and hence prevent esterase-mediated drug catalysis.

The compounds of Formula (I)-(V) may be administered either before or after (sequentially), or at the same time (simultaneously) as the drug that is metabolized by a carboxylesterase.

Formulations comprising a compound of Formula (I)-(V) and a drug, for example, CPT-11, which is metabolized by a carboxylesterase to generate, for example, a topoisomerase I inhibitor, are also envisaged.

For the potentiation of insecticides, it is necessary to have a readily bioavailable molecule that can be co-administered with the active agent. A formulation of the insect esterase inhibitor and the insecticide may be prepared. The composition of the formulation largely depends on the solubility of the compounds and their intended use e.g. as fast acting liquid forms, or slow release pellets, etc.

A constant supply of the therapeutic compound can be ensured by providing a therapeutically effective dose (i.e., a dose effective to induce metabolic changes in a subject) at the necessary intervals, e.g., daily, every 12 hours, etc. These parameters will depend on the severity of the disease condition being treated, the regimen of any other drugs being administered (such as CPT-11, for example), other actions, such as diet modification, that are implemented, the weight, age, and sex of the subject, and other criteria, which can be readily determined according to standard good medical practice by those of skill in the art.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods and compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

For the esterase inhibitor compounds of the present invention, as further studies are conducted, information will emerge regarding appropriate dosage levels for treatment of various conditions in various subjects, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally dosage levels of between 0.001 to 10 mg/kg of body weight daily are administered to mammals. Generally, for intravenous injection or infusion dosage may be lower. The dosing schedule may vary, depending on the circulation half-life, and the formulation used.

The esterase inhibitors of the present invention (or their derivatives) may be administered in conjunction with one or more additional active ingredients or pharmaceutical compositions.

EXAMPLES

The following Examples illustrate the invention, but are not limiting.

Example 1

Carboxylesterase Inhibition Assay (a) ortho-Nitrophenyl Acetate (o-NPA) as the Substrate Carboxylesterase (CE) inhibition was determined by a spectroscopic assay using o-nitrophenyl acetate (o-NPA) as a substrate. Recombinant CEs produced from expression in *Spodoptera frugiperda* Sf9 insect cells via baculovirus were purified from serum-free culture media for the enzyme inhibition studies. Enzymes were incubated in 200 µl of 50 mM Hepes (pH 7.4) containing 3 mM o-NPA. Conversion of the o-NPA to nitrophenol was monitored by measuring the change in the absorbance at 420 nm. Absorbance readings were taken every 15 seconds for 2 minutes, and data transferred to a computer data spreadsheet. Inhibitors were dissolved in dimethylsulfoxide (DMSO) and inhibition of CE activity determined by the addition of the inhibitor solution to the o-NPA reaction mixture at a concentration of 100 µM. The final DMSO concentration was always 1% or less. The Ki value (i.e., the concentration of inhibitor that will bind to half of the binding sites in the enzyme at equilibrium) was calculated for those compounds that produced a greater then 50% reduction in the rate of change of absorbance. The above procedure was then repeated using the same assay, with inhibitor concentrations ranging from 1 nM to 100 µM. Results were then transferred to Prism software (GraphPad Software, Inc., San Diego, Calif.) and Ki values determined using sigmoidal curve fits of the data. Routinely, all analyses were performed in duplicate, and Ki values determined using at least 8 inhibitor concentrations.

Ki values, determined for human small intestine carboxylesterase (hiCE), human liver carboxylesterase (hCE1), rabbit liver carboxylesterase (rCE), human acetylcholinesterase (hAcCHE), and human butyrylcholinesterase (hBuChE) for the selective human intestinal (hiCE) carboxylesterase inhibitors identified in Table 3 are set forth in Table 5:

TABLE 5

Ki Values for the Compounds Identified in Table 3, with hiCE, hCE1, hAcChE, and rCE, using o = NPA as the Substrate

| Compound Code | Ki hiCE (nM) | Ki hCE1 (nM) | Ki hAcChE (nM) | Ki hBuChE (nM) | Ki rCE (nM) | Ki (hCE1)/ Ki (hiCE) |
|---|---|---|---|---|---|---|
| 42 | 159 | >100,000 | >100,000 | | | |
| 43 | 850 | >100,000 | >100,000 | | | |
| 44 | 451 ± 39 | >100,000 | >100,000 | >100,000 | >100,000 | >220 |
| 45 | 53.3 ± 5.5 | 13,700 ± 4,870 | >100,000 | >100,000 | 1,200 ± 230 | >250 |
| 46 | 165 ± 33 | >100,000 | >100,000 | >100,000 | 319 ± 37 | >600 |
| 47 | 194 ± 23 | >100,000 | >100,000 | >100,000 | >100,000 | >500 |
| 48 | 218 ± 45 | >100,000 | >100,000 | >100,000 | >100,000 | >450 |
| 49 | 365 ± 87 | >100,000 | >100,000 | >100,000 | 3,230 ± 439 | >250 |
| 50 | 767 ± 285 | >100,000 | >100,000 | >100,000 | 739 ± 384 | >125 |
| 51 | 1,060 ± 133 | >100,000 | >100,000 | >100,000 | 1,550 ± 350 | >90 |
| 52 | 1,310 ± 176 | >100,000 | >100,000 | >100,000 | 2,000 ± 755 | >75 |
| 53 | 150 | >100,000 | >100,000 | | | |
| 54 | 320 | >100,000 | >100,000 | | | |
| 55 | 1280 | >100,000 | >100,000 | | | |
| 56 | 1524 | >100,000 | >100,000 | | | |
| 57 | 61 | >100,000 | >100,000 | | | |
| 58 | 331 | >100,000 | >100,000 | | | |
| 59 | 41.5 ± 6.5 | >100,000 | >100,000 | >100,000 | 522 ± 144 | >2,400 |

As can be seen from Table 5, Ki values of greater than 100,000 nM observed for the human liver carboxylesterase (hCE1), human acetylcholinesterase (hAcChE) and human butyrylcholinesterase (hBuChE) indicate no inhibition of these enzymes using the selective carboxylesterase inhibitors identified in Table 3. These inhibitors demonstrate inhibition of human intestinal carboxylesterase hiCE, confirming the selectivity of these molecules for inhibition of the hiCE enzyme over hCE1, hAcCHE and hBuChE.

Ki values, determined for human small intestine carboxylesterase (hiCE), human liver carboxylesterase (hCE1), rabbit liver carboxylesterase (rCE), human acetylcholinesterase (hAcCHE), and human butyrylcholinesterase (hBuChE) for other carboxylesterase inhibitors of the present invention are set forth in Table 6:

TABLE 6

Ki Values for other carboxylesterase inhibitors of the present invention, with hiCE, hCE1, and rCE, using o-NPA as the Substrate. Acetylthiocholine and butyrylthiocholine were used as substrates for hAcChE and hBuChE, respectively.

| Compound code | hiCE Ki ± SE (nM) | hCE1 Ki ± SE (nM) | rCE Ki ± SE (nM) | hAcChE Ki (nM) | hBuChE Ki (nM) |
|---|---|---|---|---|---|
| 1 | 71.5 ± 10 | 524 ± 46 | 64 ± 6.2 | >100,000 | >100,000 |
| 2 | 14.7 ± 1.9 | 45.1 ± 3.2 | 103 ± 19 | >100,000 | >100,000 |
| 3 | 21.3 ± 1.4 | 77.6 ± 5.5 | 15 ± 1.6 | >100,000 | >100,000 |
| 4 | >100,000 | >100,000 | 8.7 ± 1.3 | >100,000 | >100,000 |
| 5 | 4.1 ± 0.4 | 99.1 ± 10 | 108 ± 8.8 | >100,000 | >100,000 |
| 6 | 10.3 ± 0.6 | 175 ± 8.5 | 200 ± 60 | >100,000 | >100,000 |
| 7 | 7.9 ± 1.0 | 295 ± 9.6 | 11.9 ± 1.1 | >100,000 | >100,000 |
| 8 | 8.9 ± 0.9 | 3,300 ± 558 | 36 ± 12 | >100,000 | >100,000 |
| 9 | 72.7 ± 8.9 | >100,000 | 53.5 ± 9.4 | >100,000 | >100,000 |
| 10 | 1,730 ± 245 | >100,000 | >100,000 | >100,000 | >100,000 |
| 11 | 209 ± 50 | >100,000 | 520 ± 31 | >100,000 | >100,000 |
| 12 | 380 ± 113 | 1,690 ± 236 | 823 ± 215 | >100,000 | >100,000 |
| 13 | >100,000 | >100,000 | 2,400 | >100,000 | >100,000 |
| 14 | 30.6 ± 5.0 | 215 ± 24 | 21.7 ± 2.5 | >100,000 | >100,000 |
| 15 | >100,000 | >100,000 | 4.1 ± 0.5 | >100,000 | >100,000 |
| 16 | 167 ± 12 | 231 ± 12 | 398 ± 59 | >100,000 | >100,000 |
| 17 | 60.4 ± 6.0 | 532 ± 35 | 49.6 ± 6.8 | >100,000 | >100,000 |
| 18 | >100,000 | >100,000 | 14.1 ± 2.5 | >100,000 | >100,000 |
| 19 | 23.4 ± 3.6 | 73.5 ± 8.4 | 17.5 ± 2.7 | >100,000 | >100,000 |
| 20 | 259 ± 53 | 372 ± 99 | 47.9 ± 18 | >100,000 | >100,000 |
| 21 | 70.2 ± 1.1 | 3,410 ± 547 | 580 ± 157 | >100,000 | >100,000 |
| 22 | 22.8 ± 3.9 | 160 ± 32 | 16.2 ± 1.7 | >100,000 | >100,000 |
| 30 | 353 ± 62 | 1,650 ± 300 | 220 ± 37 | >100,000 | >100,000 |
| 31 | 18.2 ± 3.6 | 47.4 ± 6.8 | 23.9 ± 2.9 | >100,000 | >100,000 |
| 32 | 33.3 ± 6.0 | 125 ± 15 | 119 ± 20 | >100,000 | >100,000 |
| 33 | 139 ± 20 | 1,540 ± 316 | 72.1 ± 9.1 | >100,000 | >100,000 |
| 34 | 397 ± 66 | 18,100 ± 5,850 | 267 ± 30 | >100,000 | >100,000 |
| 35 | 1,200 ± 180 | >100,000 | >100,000 | >100,000 | >100,000 |
| 36 | >100,000 | >100,000 | >100,000 | >100,000 | >100,000 |
| 37 | >100,000 | >100,000 | >100,000 | >100,000 | >100,000 |
| 38 | 5.6 ± 0.4 | 8.0 ± 0.9 | 6.1 ± 0.6 | >100,000 | >100,000 |

Compound 29, whilst demonstrating inhibition of hiCE, hCE1, and rCE, also inhibited hAcChE.

(b) Irinotecan (CPT-11) as the Substrate

Since the sulphonamide compounds identified herein are competitive inhibitors of hiCE, their activity is dependant upon the substrate used. To access the ability of these compounds to inhibit the hiCE-mediated activation of CPT-11, Ki values were determined using CPT-11 as the substrate.

CPT-11 concentrations were fixed at 100 μm, and inhibitor concentrations varied from 1 nM to 10 μM. Following incubation for an hour at 37° C., the levels of SN-38 in the reaction mixture was determined by High Performance Liquid Chromatography (HPLC). Ki values for inhibition of the metabolism of CPT-11 by the sulphonamide compounds identified in Table 3, are set forth in Table 7.

TABLE 7

Ki hiCE Values for the Sulphonamide Compounds Identified in Table 3, using CPT-11 as the Substrate

| Compound Code | Ki hiCE (nM) |
|---|---|
| 44 | >100,000 |
| 45 | 141 ± 64 |
| 46 | >100,000 |
| 47 | >100,000 |
| 48 | >100,000 |
| 49 | 238 ± 29 |
| 50 | >100,000 |
| 51 | 892 ± 67 |

TABLE 7-continued

Ki hiCE Values for the Sulphonamide Compounds Identified in Table 3, using CPT-11 as the Substrate

| Compound Code | Ki hiCE (nM) |
|---|---|
| 52 | 3,220 ± 950 |
| 59 | 110 ± 23 |

As can be seen from a comparison of the date set forth in Tables 5 and 7, Ki hiCE values are approximately ten-fold higher for the inhibition of metabolism of CPT-11, than the corresponding values obtained using o-NPA as the substrate. The observed values are in the high nM range, indicating that these compounds would be effective for in vivo applications.

Example 2

Inhibition of Acetylcholinesterase and Butyrylcholinesterase

The activity of the hiCE selective carboxylesterase inhibitors identified in Table 3 toward acetylcholinesterase (AcChE) and butyrylcholinesterase metabolism was investigated. Purified AcChE was purchased from Sigma Biochemicals (St. Louis, Mo.) and substrate metabolism was monitored using a spectrophotometric assay. 1 mM acetylthiocholine was mixed with 0.5 mM of 5,5'-dithio-bis-(2-nitrobenzoic acid) in 50 mM Hepes (pH 7.4) in the presence of the inhibitor (100 µM). The reaction was initiated by the addition of 0.22 U/ml AcChE (where 1 U is the amount of enzyme that hydrolyzes µmol of acetylthiocholine iodide per min at pH 7.4 at 37° C.), and the reaction monitored by measuring the change of the absorbance at 405 nM every 15 seconds 2 minutes. Data was transferred to GraphPad Prism software, and Ki values were calculated as described in the Example above.

Purified BuChE was purchased from Sigma Biochemicals (St. Louis, Mo.) and substrate metabolism was monitored using a spectrophotometric assay. 1 mM butyrylthiocholine was mixed with 0.5 mM of 5,5'-dithio-bis-(2-nitrobenzoic acid) in 50 mM Hepes (pH 7.4) in the presence of the inhibitor (100 µM). The reaction was initiated by the addition of 0.05 U/ml BuChE (where 1 U is the amount of enzyme that hydrolyzes µmol of butyrylcholine iodide per min at pH 8.0 at 37° C.), and the reaction monitored by measuring the change of the absorbance at 405 nM every 15 seconds 2 minutes. Data was transferred to GraphPad Prism software, and Ki values were calculated as described in the Example above.

Table 5 sets forth the Ki values for human AcChE using the compounds described in Table 3. As can clearly be seen, Ki values greater than 100,000 nM indicate no inhibition of hAcChE or hBuChE by the selective human intestinal carboxylesterase inhibitors identified in Table 3.

Example 3

Ability of the Selective hiCE Inhibitors to Cross Cell Membranes

To monitor the ability of the compounds to cross the cell membrane and inhibit carboxylesterase activity intracellularly, an assay using human tumor cells expressing hiCE was devised. U373MGhiCE (a human glioma cell line transfected with a plasmid expressing hiCE) were plated in T25 flasks and allowed to grow to confluency (approximately $2\text{-}5 \times 10^5$ cells). Inhibitors were then added at a final concentration of 10 µm, and incubation allowed to continue for 1 hour. At this time, the cells were washed extensively with 5 ml of complete media and 2×5 ml of Hanks balanced salt solution, and cell extracts were prepared. Carboxylesterase activity was then determined using o-NPA as a substrate.

Table 8 sets forth the level of intracellular enzyme inhibition following incubation of human glioblastoma tumor cells expressing human intestinal carboxylesterase with 10 µM of each compound identified in Table 3.

TABLE 8

Inhibition of intracellular human intestinal carboxylesterase following incubation with 10 µM of the compound identified in Table 3.

| Compound Code | Inhibition of intracellular carboxylesterase (%) |
|---|---|
| 42 | 0 |
| 43 | ND |
| 44 | 0.6 |
| 45 | 7.5 |
| 46 | 0 |
| 47 | 9.2 |
| 48 | 8.9 |
| 49 | 7.6 |
| 50 | 14.6 |
| 51 | 5.5 |
| 52 | 9.6 |
| 53 | 3.9 |
| 54 | 0 |
| 55 | ND |
| 56 | 0 |
| 57 | 24.2 |
| 58 | 11.5 |
| 59 | 8.3 |

ND—not determined

As can be seen from Table 8, none of the selective hiCE inhibitors identified in Table 3 significantly cross cell-membranes and inhibit carboxylesterase activity intracellularly.

The present invention is not to be limited in scope by the specific embodiments described herein. Various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference.

What is claimed is:

1. A method of inhibiting an esterase in a subject in need thereof, which method comprises administering to the subject an esterase inhibiting amount of an α,β-diketone of Formula (V):

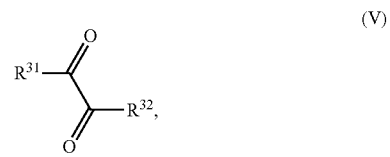

(V)

wherein
  $R^{31}$ and $R^{32}$ are each independently aryl or heteroaryl, in which the aryl or heteroaryl is optionally substituted with one or more halogen, hydroxy, $C_1$-$C_6$ linear or branched alkyl, $C_1$-$C_6$ linear or branched halo-alkyl, $C_1$-$C_6$ alkoxy, $NR^{33}R^{34}$, COOH, or $NO_2$, and the heteroaryl is a 5-membered or 6-membered ring containing O, N, or S; or $R^{31}$ and $R^{32}$ are optionally linked to form an optionally substituted polycyclic aryl or heteroaryl ring system; and $R^{33}$ and $R^{34}$ are independently hydrogen or $C_1$-$C_6$ linear or branched alkyl and
  the esterase is a human intestinal carboxylesterase.

2. The method of claim 1, wherein each of $R^{31}$ and $R^{32}$, independently, is aryl optionally substituted with one or more halogen, hydroxy, $C_1$-$C_6$ linear or branched alkyl, $C_1$-$C_6$ linear or branched halo-alkyl, $C_1$-$C_6$ alkoxy, $NR^{33}R^{34}$, COOH, or $NO_2$.

3. The method of claim 2, wherein each of $R^{31}$ and $R^{32}$, independently, is phenyl or phenyl substituted with one or more F, Br, Cl, $CH_2Br$, OH, $CH_3$, $OCH_3$, $N(CH_3)_2$, COOH, or $NO_2$.

4. The method of claim 3, wherein the α,β-diketone is selected from the group consisting of
4-[oxo(phenyl)acetyl]benzoic acid;
diphenylethane-1,2-dione;
1-[4-bromomethyl)phenyl]-2-phenylethane-1,2-dione;
1,2-bis(4-bromo-3-nitrophenyl)ethane-1,2-dione;
1-(3,4-dimethylphenyl)-2-phenylethane-1,2-dione;
1-(4-methoxyphenyl)-2-2-phenylethane-1,2-dione;
1-(4-methyl-3-nitrophenyl)-2-phenylethane-1,2-dione;
1-(2-chlorophenyl)-2-(3,4-dimethoxyphenyl)ethane-1,2-dione;
1,2-bis(5-bromo-2-hydroxyphenyl)ethane-1,2-dione;
1,2-bis(2,4-dihydroxyphenyl)ethane-1,2-dione;
1-(2,4-dinitrophenyl)-2-phenylethane-1,2-dione;
1-(pentachlorophenyl)-2-(pentafluorophenyl)ethane-1,2-dione;
1,2-bis[4(dimethylamino)phenyl]ethane-1,2-dione;
1-(4-nitrophenyl)-2-phenylethane-1,2-dione;
(1,2-bis(4-bromophenyl)ethane-1,2-dione;
1,2-bis(4-fluorophenyl)ethane-1,2-dione;
1,2-bis(4-methylphenyl)ethane-1,2-dione;
1,2-bis(4-chlorophenyl)ethane-1,2-dione;
1,2-bis(3,5-difluorophenyl)ethane-1,2-dione;
1,2-bis(3,4,5-trifluorophenyl)ethane-1,2-dione;
1,2-bis(4-methoxyphenyl)ethane-1,2-dione;
1-(4-chlorophenyl)-2-(4-methylphenyl)ethane-1,2-dione;
1,2-bis(2-chlorophenyl)ethane-1,2-dione;
1-(4-chlorophenyl)-2-phenylethane-1,2-dione;
1-(4-methylphenyl)-2-phenylethane-1,2-dione;
1,2-bis(3-methoxyphenyl)ethane-1,2-dione;
1,2-bis(3-nitrophenyl)ethane-1,2-dione;
1,2-bis(4-hydroxyphenyl)ethane-1,2-dione;
1,2-bis(4-hydroxy-3-nitrophenyl)ethane-1,2-dione; and
1,2-bis(4-methoxy-3-nitrophenyl)ethane-1,2-dione.

5. The method of claim 1, wherein each of $R^{31}$ and $R^{32}$, independently, is heteroaryl.

6. The method of claim 5, wherein each of $R^{31}$ and $R^{32}$, independently, is thienyl, furyl, or pyridinyl.

7. The method of claim 6, wherein the α,β-diketone is selected from the group consisting of
1,2-dithien-2-yl-ethane-1,2-dione;
1,2-di-2-furylethane-1,2-dione; and
1,2-dipyridin-2-ylethane-1,2-dione.

8. The method of claim 1, wherein $R^{31}$ and $R^{32}$ are linked to form an optionally substituted polycyclic aryl or heteroaryl ring system.

9. The method of claim 8, wherein $R^{31}$ and $R^{32}$ are linked to form an unsubstituted bicyclic, tricyclic, or tetracyclic aryl ring system.

10. The method of claim 9, wherein the α,β-diketone is selected from the group consisting of
aceanthrylene-1,2-dione;
phenanthrene-9,10-dione; and
acenaphthylene-1,2-dione.

11. The method of claim 1, wherein administering the α,β-diketone reduces the gastrointestinal toxicity caused by administration of a drug to the subject.

12. The method of claim 11, wherein the gastrointestinal toxicity is delayed diarrhea.

13. The method of claim 11, wherein the drug is an anti-cancer drug.

14. The method of claim 13, wherein the anti-cancer drug is CPT-11.

15. The method of claim 11, where the drug and the α,β-diketone are administered simultaneously or sequentially.

16. The method of claim 1, wherein administering the α,β-diketone treats or ameliorates the effects of an overdose of a drug metabolized by the carboxylesterase in the subject.

17. The method of claim 16, wherein the drug is selected from cocaine, heroin, meperidine, capecitabine and flumazenil.

18. A method of inhibiting an esterase in a subject in need thereof, which method comprises administering to the subject an esterase inhibiting amount of an α,β-diketone of Formula (V):

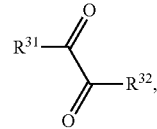

(V)

wherein
$R^{31}$ is aryl or heteroaryl, in which the aryl is substituted with one or more halogen, hydroxy, $C_1$-$C_6$ linear or branched alkyl, $C_1$-$C_6$ linear or branched halo-alkyl, $C_2$-$C_6$ alkoxy, $NR^{33}R^{34}$, or COOH; the heteroaryl is a 5-membered or 6-membered ring containing O, N, or S and is optionally substituted with one or more halogen, hydroxy, $C_1$-$C_6$ linear or branched alkyl, $C_1$-$C_6$ linear or branched halo-alkyl, $C_1$-$C_6$ alkoxy, $NR^{33}R^{34}$, COOH, or $NO_2$; and $R^{33}$ and $R^{34}$ are independently hydrogen or $C_2$-$C_6$ linear or branched alkyl;
$R^{32}$ is aryl or heteroaryl, in which the aryl or heteroaryl is optionally substituted with one or more halogen, hydroxy, $C_1$-$C_6$ linear or branched alkyl, $C_1$-$C_6$ linear or branched halo-alkyl, $C_1$-$C_6$ alkoxy, $NR^{33}R^{34}$, COOH, or $NO_2$; the heteroaryl is a 5-membered or 6-membered ring containing O, N, or S; and $R^{33}$ and $R^{34}$ are independently hydrogen or $C_1$-$C_6$ linear or branched alkyl;
or $R^{31}$ and $R^{32}$ are optionally linked to form an optionally substituted polycyclic aryl or heteroaryl ring system; and
the esterase is a human intestinal carboxylesterase.

* * * * *